United States Patent [19]
Bodor et al.

[11] Patent Number: 4,764,381
[45] Date of Patent: Aug. 16, 1988

[54] PERCUTANEOUS PENETRATION ENHANCER OF OLEIC ACID AND 2-ETHYL-1, 3-HEXANEDIOL

[75] Inventors: Nicholas Bodor, Gainesville, Fla.; Thorsteinn Loftsson, Reykjavik, Iceland

[73] Assignee: Key Pharmaceuticals, Inc., Kenilworth, N.J.

[21] Appl. No.: 806,257

[22] Filed: Dec. 6, 1985

[51] Int. Cl.$^4$ .................. A61L 15/03; A61F 13/00; A61K 9/06; A61K 31/21
[52] U.S. Cl. .................. 424/449; 514/509; 514/947
[58] Field of Search ............ 424/449; 514/947, 509

[56] References Cited

U.S. PATENT DOCUMENTS

| | | | |
|---|---|---|---|
| 4,322,433 | 3/1982 | Leslie et al. | 514/970 |
| 4,557,934 | 12/1985 | Cooper | 514/635 |
| 4,605,548 | 8/1986 | Ushiyama et al. | 424/449 |
| 4,654,209 | 3/1987 | Leslie et al. | 514/947 |

OTHER PUBLICATIONS

Cooper et al., I CA. 103 #59235d(1985) of J. Pharm. Sci. 74(6): 688–9 (1985).
Bennett et al., CA. 103 #27200x(1985) of J. Pharm. Pharmacol. 37(5).298–304 (1985).
Yamada et al., CA. 102 #100807m(1985) of EPO 127468 Dec. 5, 1984 17 pp.
Uda et al., CA. 102 #100808n(1985) of EPO 127426 Dec. 5, 1984 19 pp.
Cooper II CA. 102 #119657j(1985) of EPO 129285 Dec. 27, 1984 60 pp.
Cooper, III CA. 100 #91365v(1984) of EPO 95813 Dec. 7, 1983 23 pp.
Cooper et al., II CA. 102 #84443g 1985 of EPO 129283 Dec. 27, 1984 40 pp.
Wickett et al., CA. 96 #187298a 1982 of EPO 43738 Jan. 13, 1982 39 pp.

*Primary Examiner*—Shep K. Rose
*Attorney, Agent, or Firm*—John J. Maitner; Stephen I. Miller; James R. Nelson

[57] ABSTRACT

Pharmaceutical preparations comprised of a pharmaceutically active ingredient and a carrier which comprises a percutaneous penetration enhancer comprised of 2-ethyl-1, 3-hexanediol alone or in combination with oleic acid is disclosed. The 2-ethyl-1, 3-hexanediol may be present in an amount in the range of about 50% to 100% based on the weight of the carrier. The oleic acid may be used in combination with 2-ethyl-1, 3-hexanediol in an amount of about 1 to 40% based on the weight of the carrier to provide a synergistic effect with respect to percutaneous penetration enhancement. The compound 2-ethyl-1, 3-hexanediol as used alone and/or in combination with the oleic acid has been found to significantly enhance the delivery of a drug, to a patient, from a transdermal delivery system.

1 Claim, No Drawings

PERCUTANEOUS PENETRATION ENHANCER OF OLEIC ACID AND 2-ETHYL-1, 3-HEXANEDIOL

FIELD OF THE INVENTION

The present invention relates to the field of pharmaceutical preparations which are applied to the skin in order to obtain transdermal delivery of a pharmaceutically active drug from the preparation to the patient. More specifically, the invention relates to such preparations which utilize as a percutaneous penetration enhancer 2-ethyl-1, 3-hexanediol alone and/or in combination with oleic acid.

BACKGROUND OF THE INVENTION

It is well known that many drugs taken orally, are destroyed on the first pass through the liver. It is also well known that when many drugs are taken orally, their rate of absorption into the body is not constant. In view of such difficulties, a number of different drug delivery systems have been developed. Recently, the use of transdermal delivery systems have met with increasing interest by researchers in the pharmaceutical drug delivery field.

U.S. Pat. No. 4,291,015 to Keith, et al., discloses the use of a polymeric diffusion matrix for the sustained release of pharmaceutically active drugs. The matrix is covered by a backing layer and applied to the skin where diffusion of the pharmaceutically active drug occurs and the drug is transdermaley delivered to the patient. Although U.S. Pat. No. 4,291,015 discloses transdermal delivery of nitroglycerine, other drugs may be delivered by utilizing the same or a similar matrix, as disclosed in U.S. Pat. Nos. 4,292,820; 4,292,302; and 4,292,303.

U.S. Pat. No. 4,490,206 discloses the use of a different type of transdermal delivery system whereby the pharmaceutically active drug is dispersed within an adhesive (see also U.S. Pat. No. 4,390,520). In accordance with such systems, the pharmaceutically active drug is dispersed in a pressure-sensitive adhesive which is adhered to the skin. The drug then diffuses from the adhesive through the skin for delivery to the patient. Other types of transdermal delivery systems are also known and each has various advantages and disadvantages with respect to the transdermal delivery of different types of pharmaceutically active drugs.

One of the problems with utilizing transdermal delivery systems is one of efficacy. More specifically, the device must supply a sufficient amount of the pharmaceutically active ingredient to the patient to obtain the desired pharmaceutical effect on the patient over a given period of time. Different means may be employed in order to obtain the desired efficacy over that period of time.

One means of attempting to increase the amount of drug delivery might be to include a higher concentration of the pharmaceutically active drug in the delivery system. By simply increasing the concentration of the drug, the amount of the drug delivered to the patient would hopefully be increased. This concept might work well to a certain extent but would be limited by the amount of drug which can be delivered through the skin barrier, i.e., the skin acts as a rate limitation means.

Another means for increasing the amount of drug delivered and obtaining the desired efficacy, might involve increasing the surface area contact of the delivery system with the skin. Although an increase in the surface area will increase the amount of drug delivered to the patient, there are, of course, practical limitations with respect to increasing this surface area. The cost of producing very large delivery systems might be prohibitive. Patients would be unlikely to ware a delivery system which had a surface such that it covered the entire back and/or front of the patient.

A completely different concept for increasing transdermal delivery of a pharmaceutically active drug is the utilization of a penetration enhancer to be used in combination with the drug delivery system. Utilization of such enhancers is subject to certain limitations such as the fact that the enhancer must be determatologically acceptable, and compatible with the pharmaceutically active drug as well as the delivery system which it is used in connection with.

Perhaps the most famous of such penetration enhancers is "DMSO (Dimethyl sulfoxide)". However, DMSO has not received FDA approval for use on humans. Another well known penetration enhancer is AZONE, see U.S. Pat. Nos. 3,909,816; 4,311,481; and 4,316,893 as well as the corresponding foreign patents.

More recently, there has been some teachings with respect to the use of oleic acid as a penetration enhancer. (See Cooper, Eugene, R., "Increased Skin Permeability for LITOTHILIC Molecules" Journal of Pharmaceutical Sciences, volume 73, number 8, August 1984.) Cooper discloses the use of oleic acid in different concentrations in the presence of propylene glycol as a solid. The oleic acid does appear to enhance penetration of the active ingredient SALICYLIC acid. Cooper also discloses the use of oleic acid in combination with 1,2-butanediol. The article specifically indicates that "other diols also exhibit this synergism with lipids, but the effect is less pronounced as the chain length is increased". Cooper teaches that the treatment of the skin with surfactants can have a substantial influence on increasing the penetration of polar molecules. However, such surfactants do not generally increase the transdermal penetration of the non-polar molecules. Accordingly, Cooper concludes that the enhanced transdermal penetration of non-polar molecules such as salicylic acid can be obtained by the addition of small amounts of fatty acids or alcohols to the formulation. More specifically transdermal penetration of salicylic acid can be greatly enhanced by the addition of small amounts of oleic acid. Accordingly, Cooper appears to teach only the use of small amounts of oleic acid either alone or in combination with diols of short chain length and contains no teachings with respect to the use of large amounts of oleic acid alone or in combination with long chain diols and actually teaches against the use of such long chain diols.

U.S. Pat. No. 4,305,936 discloses a solution for topical or local application comprised of a corticosteroid in a carrier. The carrier is comprised of 1 to 4% by weight of solubilizing agents of a glyceral ester of a fatty acid containing 6 to 22 carbon atoms, 10 to 50% by weight of an alkanol cosolvent and from 20 to 50% by weight of water. The patent also indicates that the carrier can include a carrier a "suitable auxiliary adjuvant in an amount of up to 10% by weight." Oleic acid is mentioned as a suitable auxiliary adjuvant. The patent does not appear to contain any teaching with respect to the effect oleic acid might have on enhancing penetration and does not appear to contain any teachings with respect to the use of large amounts of oleic acid alone or in combination with a long chain diol.

U.S. Pat. No. 4,455,146 discloses a plaster comprised of a thermalplastic elastomer, an oil or higher fatty acid, a tack-providing resin and an active ingredient. The "higher fatty acid" may be present in the range of 25 to 370 parts by weight per 100 parts by weight of the thermalplastic elastomer. The active ingredient may be present in an amount in the range of 0.09 to 110 parts by weight per 100 parts by weight of the thermalplastic elastomer, (see column 4, lines 3–35). Oleic acid is mentioned as "one of the preferred" higher fatty acids, (see column 3, lines 16–17).

Although percutaneous penetration enhancers are known, there remains a need for an enhancer which is dermatologically acceptable has FDA approval for use on human skin and has a substantial effect on increasing in the rate of transdermal delivery of a pharmaceutically active drug to a patient.

SUMMARY OF THE INVENTION

The present invention provides a pharmaceutical preparation in the form of a transdermal delivery system comprised of a carrier having dispersed therein a pharmaceutically active drug. The carrier is comprised of a percutaneous penetration enhancer which includes 2-ethyl-1, 3-hexanediol (hereinafter EHD) alone and/or in combination with oleic acid. The present inventor has found that the use of high concentrations of EHD as a carrier can have a substantial effect on increasing in the rate of delivery of pharmaceutically active drugs and has further found that rate of delivery is further enhanced, and a synergistic effect is obtained, when the oleic acid is used in combination with EHD. The percutaneous penetration enhancement of this combination has been found to work particularly well in connection with pharmaceutically active drugs such as vasodiolators e.g., nitroglycerine, anti-arythmias e.g., lidocane; sterioids e.g., estrogen and corticosteroids.

It is a primary object of this invention to provide a percutaneous penetration enhancer for use in connection with a transdermal delivery system.

Another object of this invention is to provide such a penetration enhancer which is comprised of a large percentage of EHD alone and/or in combination with oleic acid.

Still another object of this invention is to provide a transdermal delivery system using EHD in an amount of 50% to 100% based on the weight of the carrier as a penetration enhancer.

Another object of this invention is to provide a transdermal delivery system comprised of a pharmaceutically active ingredient and a carrier which carrier is comprised of EHD in an amount of 50% or more by weight and oleic acid in an amount of 1 to 40% by weight based on the weight of the carrier.

Yet another object of this invention is to provide a transdermal delivery system comprised of nitroglycerine and a carrier wherein the carrier is comprised of 50% or more by weight of EHD and about 5% by weight of oleic acid.

DETAILED DESCRIPTION OF THE INVENTION

In order for a compound to be useful as a percutaneous penetration enhancer the compound must meet a number of different requirements. Firstly, the compound must be a dermatologically acceptable compound which when used topically on the skin does not cause adverse side effects. Secondly, the compound must be compatible with the active ingredient within the transdermal delivery system. If the compound and the active ingredient are incompatible then a separation will take place or a reaction could occur which would destroy the pharmacological activity of the active ingredient. Thirdly, it is preferable for the compound to have been approved for use on humans by the Food And Drug Administration of the United States. Further, the compound must of course have a substantial effect on increasing the transdermal rate of delivery of the pharmaceutically active drug.

The present inventor investigated a large number of compounds in order to find one or more compounds which would meet the above referred to criteria and be useful as a percutaneous penetration enhancer. One such compound investigated was EHD which is known to be useful as an insect repellent. In addition to being used as an insect repellent, EHD has been used in an antibacterial and an antifungal composition as disclosed by Minuto in U.S. Pat. No. 4,241,084. This patent discloses a pharmaceutical composition which includes an antibacterial - antifungal composition dispersed in other components which may include EHD. The composition may be applied to the skin for the topical application of the antibacterial and antifungal compositions.

Another compound investigated by the present inventor was oleic acid. Oleic acid has been used as a vehicle in which salicylic acid and carbinoxamine have been incorporated. See "Percutaneous Absorption Of Drugs From Oily Vehicles" Washitake, et al., Journal of Pharmaceutical Sciences, volume 64, number 3, pages 397–401. Further, oleic acid has been disclosed as being used in connection with a salicylic acid as indicated above by Cooper. The publication by Washitake, et al., demonstrates that the effect of oleic acid varies depending on the active ingredient which is included with the oleic acid. Therefore, it is not possible to accurately predict which pharmaceutically active compounds might have their skin penetration enhanced by the use of oleic acid.

EXAMPLE 1

Nineteen different compositions were prepared containing 10% nitroglycerine each. The composition of the carrier within each of the nineteen different compositions is shown below in Table I.

TABLE I

| | Diffusion of Nitroglycerine Through Hairless Mouse Skin Vehicle Composition, ml[1] | | | | | | | | |
|---|---|---|---|---|---|---|---|---|---|
| | | | | | 10% | | | | |
| NTG/PG[2] | PG | DET | DMSO | DTP | EHD | FSB | H$_2$O | OA | UREA |
| 1. 2 | 2 | 2 | | | | | | | |
| 2. 1 | 4 | | | | | | | | |
| 3. 4 | | | | | | | | | |
| 4. 2 | 1 | | | | 1 | | | | |
| 5. 2 | 1 | 1 | | | | | | | |

TABLE I-continued

Diffusion of Nitroglycerine Through
Hairless Mouse Skin Vehicle Composition, ml[1]

| | NTG/PG[2] | PG | DET | DMSO | DTP | EHD | FSB | H$_2$O | OA | UREA |
|---|---|---|---|---|---|---|---|---|---|---|
| 6. | 2 | 0.5 | 1 | | | | | 0.5 | | 100 mg |
| 7. | 2 | | | | | 1 | 200 mg | 1 | | |
| 8. | 2 | | | | | 1.8 | 55 mg | 0.2 | | |
| 9. | 2 | | | | | 1.8 | | 0.2 | | 410 mg |
| 10. | 1 | 2 | | | | 1 | | 1 | | |
| 11. | 1 | 1 | | | | 2 | | 1 | | |
| 12. | 1 | 1 | | | | 2 | | 1 | | 300 mg |
| 13. | 1 | 3 | | | | | | 1 | | |
| 14. | 1 | 1 | | | | 2 | 100 mg | 1 | | |
| 15. | 1 | 0.8 | | | | | | | 0.2 | |
| 16. | 1 | 0.9 | | | | | | | 0.1 | |
| 17. | 1 | 0.7 | | | | | | | 0.3 | |
| 18. | 1 | 0.8 | | 0.2 | | | | | | |
| 19. | 1 | 0.8 | | | 0.2 | | | | | |

[1]except for the oleic acid experiments when 0.5 ml was used, 1 ml donor phase was applied to each skin.
[2]10% NTG/PG = Lot SDM no. 27, A 27-4, ICI
PG = propylene glycol
DET = N,N—diethyl-m-toluamide
DTP = 1,3-dimethyl-3,4,5,6 tetrahydro-2(1H) pryimidinone After preparing each of these nineteen different compositions the compositions were tested to determine the effect of all of the compounds on enhancing the percutaneous penetration of nitroglycerine through hairless rat skin. The results of these test for all nineteen compositions are shown within Table 11.

TABLE II

| | Mg NTG/skin | Flux[1] ± s.d. | Lag Time | N |
|---|---|---|---|---|
| 1. | 0.05 | 0.044 ± 0.032 | 2.7 ± 0.56 | 6 |
| 2. | 0.02 | 0.0074 ± 0.006 | 1.86 ± 1.38 | 5 |
| 3. | 0.1 | 0.022 ± 0.003 | 1.85 ± 0.28 | 4 |
| 4. | 0.05 | 0.021 | 2.23 | 2 |
| 5. | 0.05 | 0.007 | 2.57 | 2 |
| 6. | 0.05 | 0.010 | 1.41 | 2 |
| 7. | 0.05 | 0.032 | | 2 |
| 8. | 0.05 | 0.012 | | 2 |
| 9. | 0.05 | 0.012 | | 2 |
| 10. | 0.02 | 0.019 | 1.52 | 2 |
| 11. | 0.02 | 0.015 ± 0.005 | 1.48 ± 0.47 | 6 |
| 12. | 0.02 | 0.024 | 1.85 | 2 |
| 13. | 0.02 | 0.022 ± 0.003 | 1.51 ± 0.06 | 4 |
| 14. | 0.02 | 0.017 ± 0.003 | 1.51 ± 0.13 | 4 |
| 15. | 0.05 | 0.306 ± 0.084 | 1.11 ± 0.41 | 8 |
| 16. | 0.05 | 0.360 ± 0.089 | 1.65 ± 0.46 | 6 |
| 17. | 0.05 | 0.351 ± 0.034 | 1.70 ± 0.08 | 3 |
| 18. | 0.05 | 0.032 ± 0.004 | 2.84 ± 0.81 | 3 |
| 19. | 0.05 | 0.039 ± 0.019 | 2.53 ± 0.23 | 3 |

[1]flux measured in mg/cm$^2$ hr for times up to 10 hours

The data within Table II clearly shows that the oleic acid utilized as the percutaneous penetration enhancer in compositions 15, 16, and 17 greatly increased the flux through the hairless mouse skin.

EXAMPLE 2

After determining that oleic acid had a substantial influence on enhancing the penetration of nitroglycerine through hairless mice skin the present inventor had experiments carried out in order to determine the amount of oleic acid which could be utilized in order to most efficiently enhance the penetration. The results of those experiments are summarized in Table III.

TABLE III

Oleic Acid Concentration In Vehicle:
Nitroglycerine Flux through Hairless Mouse Skin

| Oleic Acid | Flux, mg/cm$^2$ hr | n |
|---|---|---|
| 0 | 0.046 ± 0.021 | 9 |
| 5 | 0.360 ± 0.089 | 6 |

TABLE III-continued

Oleic Acid Concentration In Vehicle:
Nitroglycerine Flux through Hairless Mouse Skin

| Oleic Acid | Flux, mg/cm$^2$ hr | n |
|---|---|---|
| 10 | 0.306 ± 0.084 | 8 |
| 15 | 0.351 ± 0.034 | 3 |

The results shown within Table III indicate that the flux of the nitroglycerine across the hairless mouse skin is not increased much by increasing the amount of oleic acid beyond 5% by weight based on the total weight of composition.

After determining the usefulness of oleic acid as a percutaneous penetration enhancer the present inventor carried out experimentation in order to determine if the combination of two or more different compounds might have some synergistic effect with respect to enhancing penetration of one or more active ingredients. As a result, the present inventor did find that the addition of minor amounts of oleic acid to major amounts of EHD had a synergistic effect with respect to the percutaneous penetration enhancement of pharmaceutically active ingredients. Information describing experiments and the results obtained were put forth below.

EXAMPLE III

Diffusion of Triamcinolone Acetonide Through Hairless Mouse Skin

Solutions of Triamcinolone Acetonide (TA) (RD-2K-0537) in propylene glycol (PG), 2-ethyl, 1,3 hexanediol (EHD), and 5% oleic acid (OA) in EHD were used to measure the flux in mg/cm$^2$hr of the compound through hairless mouse skin. When a 0.5% solution of the compound in 5% OA/EHD was applied, the flux was about four times greater than that from a 0.5% solution in PG and twice that of a 0.5% solution in EHD. Similarly, 5% OA/EHD was almost twice as effective as EHD alone when a 0.1% solution was used. This solvent gave results about twelve times better than PG alone at this concentration.

Experimental

Skins from female hairless mice, strain SKH1HR-1 (Temple University) were placed over circular teflon holders and secured with O-rings. The holders were attached to Plexiglas reservoirs filled with a receptor phase consisting of 39 ml of 2% Brij 58 (polyoxethylene 20 cetyl either, Sigma) dissolved in pH 7.4 isotonic phosphate buffer and 0.4 ml formalin. The solution was degassed before use. 500 l aliquots of the test solutions were spread over each skin. The diffusion cells were stirred for 48 hrs in a 35° incubator and 1 ml samples were removed at intervals and frozen until analyzed.

The samples were analyzed by HPLC using a Waters 481 variable wavelength UV detector set at 20 nm, LDC constametric III pump at 1 ml/min flow, and Fisher Recordall recorder at chart speed 0.25 cm/min. Using a C-18 column and 50% acetonitrile in distilled water triamcinolone had a retention of 1.4 cm.

TABLE IV
Results
The Flux of TA in Each of Three Solvents

|  | 0.1% TA | 0.5% TA |
|---|---|---|
| PG | $2.04 + 1.4 \times 10^{-5}$ | $2.49 + 0.88 \times 10^{-4}$ |
| EHD | $1.49 + 0.39 \times 10^{-4}$ | $5.35 + 2.00 \times 10^{-4}$ |
| 5% OA/EHD | $2.57 + 0.56 \times 10^{-4}$ | $1.06 + 0.39 \times 10^{-3}$ |

Diffusion of Estradiol Through Hairless Mouse Skin

Estradiol was mixed with an assortment of diffusion enhancing substances in an attempt to increase its flux through skin. The compound was also mixed with its ester, estradiol 17- cypionate, to achieve the same result. Since estradiol is not especially water soluble the receptor phase was varied to include different amounts of a surfactant or plasma to better dissolve any diffused estradiol which might be attached to the underside of the skin.

Experimental

Female hairless mice, strain SKHI-R-1 (Temple University) were killed by cervical dislocation. The skins were removed, placed carefully over a circular teflon holder, and held in place with an O-ring. This yielded a 7.07 cm² skin surface which was suspended over a plexiglas reservoir (Kersco Engineering, Palo Alto, Calif.) containing 39 ml of receptor phase: ph 7.4 phosphate buffer with or without 2% Brij-58 (polyoxyethylene 20 cetyl ether) or plasma. The receptor phase was filtered under a vacuum to remove dissolved air. Estradiol 100 mg, or 100 mg estradiol plus 100 mg estradiol 17- -cypionate, was powdered and mixed with 2 ml of the desired vehicle. The resulting suspension was sonicated and 0.5 ml spread over each skin. The cells were stirred overnight in a 35° C. incubator and 1 ml samples taken at 6 hr intervals. Samples were pipetted into 1 ml $CH_3CN$ to dissolve all diffused estradiol.

The samples were analyzed by HPLC using a Beckman model 160 detector at 280 nm. Mobile phase was 55% $CH_3CN$ in distilled water. At a flow of 1 ml/min and chart speed 0.5 cm/min estradiol retention was 2.95 cm.

Results:

Table I summarizes 33 experiments using estradiol alone mixed with different combinations of 15 vehicle additives. Fair results were obtained with vehicles which contained 2-ethyl-1,3-hexanediols (EHD) or, N,N'-diethyl-m-toluamide (DET) and oleic acid (OA) or methyl salicylate (m-Sal); total flux through skin was $1.1-1.6\times10^{-3}$ mg/cm hr.

Several experiments were conducted using a combination of estradiol and its 17- cypionate ester using combinations of nine vehicle additives (Table 2). Total flux was not changed dramatically over that found when estradiol alone was used. The flux of estradiol observed when estradiol 17- cypionate alone was applied to skin was considerably lower (Table III).

The results using different receptor phases are shown in Table IV. None of the conditions are significantly different from the others.

Conclusion:

Using DET, EHD, m-Sal or OA in the vehicle seems to give best results for the diffusion of estradiol through hairless mouse skin. Attempts to increase the flux by adding an ester to the donor phase or by making the receptor phase more lipophilic were not successful.

TABLE V

Vehicle Composition and Flux of Estradiol through Skin after Application of Estradiol-Estradiol Cypionate Mixture

| % of Vehicle[1] | | | | | | | | | Flux, mg/cm hr | N |
|---|---|---|---|---|---|---|---|---|---|---|
| DET | DMSO | DTP | EHD | IPM | OA | m-Sal | MO | PMS | | |
|  |  |  | 100 |  |  |  |  |  | $1.49 \times 10^{-3} \pm 0.4$ | 17 |
|  |  |  | 95 |  | 5 |  |  |  | $9.23 \times 10^{-4} \pm 0.24$ | 9 |
|  |  |  | 90 |  | 10 |  |  |  | $2.15 \times 10^{-3} \pm 0.23$ | 3 |
|  |  |  | 75 |  | 25 |  |  |  | $1.27 \times 10^{-3} \pm 0.12$ | 3 |
|  |  |  | 60 |  | 40 |  |  |  | $1.36 \times 10^{-3} \pm 0.81$ | 3 |
|  |  |  | 57 |  | 43 |  |  |  | $6.08 \times 10^{-4} \pm 0.39$ | 12 |
|  |  |  | 40 |  | 60 |  |  |  | $1.14 \times 10^{-3} \pm 0.17$ | 3 |
| 33 |  |  |  | 50 |  | 17 |  |  | $3.22 \times 10^{-4} \pm 1.12$ | 8 |
|  | 10 |  | 90 |  |  |  |  |  | $7.68 \times 10^{-4} \pm 1.14$ | 6 |
|  |  | 10 | 90 |  |  |  |  |  | $9.89 \times 10^{-4} \pm 0.16$ | 5 |
|  |  |  | 95 |  |  |  |  | 5 | $1.41 \times 10^{-3} \pm 0.62$ | 6 |
|  |  |  |  |  |  |  | 100 |  | $2.9 \times 10^{-5} \pm 3.03$ | 3 |
|  |  |  |  |  |  |  | 50 |  | $4.29 \times 10^{-4} \pm 0.81$ | 3 |
|  |  |  | 45 | 5 |  |  | 50 |  | $1.34 \times 10^{-3} \pm 0.06$ | 3 |

[1]DET, N,N¹diethyl-m-toluamide
DMSO, dimethyl sulfoxide
DTP, 1,3-dimethyl-3,4,5,6 tetrahydro-2(IH)pyrimidinone
EHD, 2-ethyl-1,3-hexanediol
IPM, isopropyl myristate
OA, oleic acid
m-Sal, methyl salicylate
MO, mineral oil
PMS, polymethionine sulfoxide The present inventor determined that oleic acid could not be utilized in connection with pharmaceutically active ingredients which ingredients were a base. Accordingly, the present inventor carried out experiments in order to test the ability of EHD on enhancing the penetration of a pharmaceutically active ingredient which acted as a base such as local anesthetics. The results of these experiments are shown below within Example 4.

EXAMPLE 4

TABLE VI

| | | | Local Anesthetics: Experimental Conditions | | | | | | | | |
|---|---|---|---|---|---|---|---|---|---|---|---|
| | | | % of Vehicle[3] | | | | | | | | |
| Exp. # | Drug mg[1] | mg on skin | IPM | n-p | PG | DEA | DET | EDH | 10 N KOH/ MEOH | Sal | Vol App. ml* | # of ani. |
| L-1 | 39.3$_L$ | 5.24 | 100[2] | | | | | | | | .20 | 4 |
| L-2 | 136$_L$ | 34.0 | 67 | | | | 33 | | | | .15* | 4 |
| L-3 | 151.5$_E$ | 37.9 | 67 | | | | 33 | | | | .15* | 2 |
| L-4 | 155.6$_B$ | 38.9 | 67 | | | | 33 | | | | .15 | 2 |
| L-5 | 200.9$_E$ | 50.2 | | 34 | | 33 | 33 | | | | .15 | 2 |
| L-6 | 204.5$_B$ | 27.9 | | 64 | | 18 | 18 | | | | .15 | 2 |
| L-7 | 152$_E$ | 45.6 | | | 100 | | | | | | .18 | 2 |
| L-8 | 128.6$_B$ | 38.6 | | | 100 | | | | | | .18* | 2 |
| L-9 | 206.8$_B$ | 41.4 | | | 43 | | | 43 | 14 | | .18 | 3 |
| L-10 | 205.1$_E$ | 52.7 | | | 43 | | | 43 | 14 | | .18 | 3 |
| L-11 | 406.3$_E$ | 110.8 | | | 38 | | | 38 | 8 | 15 | .3 | 4 |
| L-12 | 428.7$_B$ | 98.9 | | | 38 | | | 38 | 8 | 15 | .3 | 4 |
| L-13 | 207.1$_E$ | 53.3 | | | | | | 86 | 14 | | .18 | 3 |
| L-14 | 208.8$_B$ | 53.7 | | | | | | 86 | 14 | | .18 | 3 |

[1]B, Bupivacaine.HCl
E, Etidocaine.HCl
L, Lidocaine.HCL.H$_2$O
[2]10% IPM in acetone
*suspension
[3]IPM, isoprypyl myristate
n-p, normal propanol
PG, propylene glycol
DEA, diethanolamine
DET, N,N—diethyl-m-toluamide
EHD, 2-ethyl-1,3-hexanediol
KOH/MeOH, potassiumhydroxide/methanol
m-Sal, methyl salicylate

TABLE VII

| | Local Anesthetics: Results | |
|---|---|---|
| Exp. # | Flux ± S.D. mg/cm$^2$ hr | Lag time ± S.D., hrs |
| L-12 | 9.67 ± .295 × 10$^{-1}$ | 5.6 ± 0.2 |
| L-11 | 4.7 ± .179 × 10$^{-1}$ | 3.8 ± 1.6 |
| L-9 | 1.46 ± 0.01 × 10$^{-1}$ | 6.5 ± 0.2 |
| L-3 | 1.43 × 10$^{-1}$ | 3.2 |
| L-10 | 6.97 ± 0.49 × 10$^{-2}$ | 6.6 ± 0.1 |
| L-2 | 5.62 ± 0.01 × 10$^{-2}$ | 2.9 |

TABLE VII-continued

| | Local Anesthetics: Results | |
|---|---|---|
| Exp. # | Flux ± S.D. mg/cm$^2$ hr | Lag time ± S.D., hrs |
| L-14 | 3.09 ± 1.46 × 10$^{-2}$ | 9.1 ± 0.2 |
| L-13 | 2.66 ± 0.65 × 10$^{-2}$ | 6.3 ± 0.1 |
| L-4 | 1.55 × 10$^{-2}$ | 4.3 |
| L-6 | 1.45 × 10$^{-2}$ | 5.2 |
| L-7 | 4.14 × 10$^{-3}$ | 6.4 |
| L-8 | 3.15 × 10$^{-3}$ | 5.2 |
| L-5 | 1.01 × 10$^{-3}$ | 3.4 |
| L-1 | 4.65 ± 0.1 × 10$^{-4}$ | 0 |

Further experimentation was then carried out in order to test the ability of certain compounds to enhance the penetration of estradiol. The results of these experiments are put forth below in Table III.

TABLE VIII

| Vehicle Composition and Flux of Estradiol through Skin | | | | | | | | | | | | | |
|---|---|---|---|---|---|---|---|---|---|---|---|---|---|
| % of Vehicle or mg solid added[1] | | | | | | | | | | | | | |
| IPM | n-P | PG | Brij 58 | DEA | DET | DOS | EHD | H$_2$O | FSB | OA | m-Sal | SLS | Urea | Flux, mg/cm$^2$ hr |
| 67 | | | | | 33 | | | | | | | | | 1.4 × 10$^{-6}$ |
| 50 | | | | | 33 | | | | | | 17 | | | 1.51 × 10$^{-3}$ |
| 50 | | | | | | | 50 | | | | | | | 4.27 × 10$^{-4}$ |
| 57 | | | | | | | | | | 43 | | | | 3.8 × 10$^{-4}$ |
| 50 | | | | | | | | | | | 17 | | | 1.3 × 10$^{-3}$ |
| | 100 | | | | | | | | | | | | | 1.4 × 10$^{-4}$ |
| 50 | | | | | | | | | | | 17 | | | 1.16 × 10$^{-3}$ |
| | | 75 | | | 25 | | | | | | | | | 4.93 × 10$^{-4}$ |
| | | 70 | | | 30 | | | | | | | | | 1.2 × 10$^{-3}$ |
| | | 50 | | | 50 | | | | | | | | | 6.59 × 10$^{-4}$ |
| | | 25 | | | 75 | | | | | | | | | 6.66 × 10$^{-4}$ |
| | | 80 | | 20 | | | | | | | | | | 1.29 × 10$^{-4}$ |
| | | 50 | | | | | | | | | | | | 4.62 × 10$^{-4}$ |
| | | 25 | | 25 | 25 | | | | | | | | | 4.52 × 10$^{-4}$ |
| | | 40 | | 20 | 40 | | | | | | | | | 5.88 × 10$^{-4}$ |
| | | 48 | | 5 | 47 | | | | | | | | | 4.26 × 10$^{-4}$ |
| | | 50 | 75.4 mg | | | | 50 | | | | | | | 1.43 × 10$^{-4}$ |
| | | 50 | | | | 118.4 mg | 50 | | | | | | | 2.14 × 10$^{-4}$ |
| | | 50 | | | | | 50 | | | | | 39.6 mg | | 6.96 × 10$^{-5}$ |
| | | | 50 | | | | 50 | | | | | | | 4.62 × 10$^{-4}$ |
| | | | 57 | | | | | | | 43 | | | | 8.36 × 10$^{-4}$ |

TABLE VIII-continued

Vehicle Composition and Flux of Estradiol through Skin
% of Vehicle or mg solid added[1]

| IPM | n-P | PG | Brij 58 | DEA | DET | DOS | EHD | H$_2$O | FSB | OA | m-Sal | SLS | Urea | Flux, mg/cm$^2$ hr |
|---|---|---|---|---|---|---|---|---|---|---|---|---|---|---|
| | 23 | 23 | | | 38 | | | 15 | | | | | 100 mg | 4.47 × 10$^{-4}$ |
| | 20 | 34 | | | | | 33 | 13 | 50 mg | | | | | 2.32 × 10$^{-4}$ |
| | 20 | 34 | | | 33 | | | 13 | 50 mg | | | | | 3.67 × 10$^{-4}$ |
| | 23 | 23 | | | | | 38 | 15 | | | | | 100 mg | 5.22 × 10$^{-5}$ |
| | | | | | 100 | | | | | | | | | 2.5 × 10$^{-4}$ |
| | | | | | | | | | | 100 | | | | 5.55 × 10$^{-4}$ |
| | | | | | | | | | | | 100 | | | 8.23 × 10$^{-4}$ |
| | | | | | 29 | | | | | 71 | | | | 6.18 × 10$^{-4}$ |
| | | | | | 57 | | | | | 43 | | | | 1.59 × 10$^{-3}$ |
| | | | | | | | 29 | | | 71 | | | | 9.0 × 10$^{-4}$ |
| | | | | | | | 57 | | | 43 | | | | 6.38 × 10$^{-4}$ |
| | | | | | 33 | | | | | | 50 | 17 | | 1.05 × 10$^{-3}$ |

[1]IPM, isopropyl myristate
n-P, normal propanol
PG, propylene glycol
Briji-58, polyoxyethylene 20 cetyl ether
DEA, diethanolamine
DET, N,N—diethyl-m-toluamide
DOS, dioctysulfosuccinate
EHD, 2-ethyl-1,3-hexanediol
FSB, formaldehyde sodium bisulfite
OA, oleic acid
m-Sal, methyl salicylate
SLS, sodium lauryl sulfate The results shown within Table VIII clearly indicate that oleic acid and EHD can increase the flux of estradiol through skin.

The present invention has been disclosed and described herein in what is believed to be its preferred embodiments. It is recognized, however, that those skilled in the art may contemplate variations thereof which are not specifically disclosed herein, which variations are intended to be encompassed by the scope of the present invention. Accordingly, the scope of the present invention should not be construed as being limited to the above description.

What is claimed:
1. A transdermal delivery system, consisting essentially of:
   nitroglycerine; and
   a carrier which consists of 1 to 10% by weight of oleic acid based on the weight of the carrier.

* * * * *